United States Patent [19]

Benvenga et al.

[11] Patent Number: 5,972,932
[45] Date of Patent: Oct. 26, 1999

[54] ANESTHETIC METHOD AND COMPOSITION

[75] Inventors: Mark J. Benvenga; Harlan E. Shannon, both of Carmel, Ind.

[73] Assignee: Eli Lilly and Company, Indianapolis, Ind.

[21] Appl. No.: 08/823,459

[22] Filed: Mar. 24, 1997

Related U.S. Application Data

[60] Provisional application No. 60/014,120, Mar. 25, 1996.

[51] Int. Cl.⁶ .......................... A61K 31/55; A61K 31/44; A61K 31/24; A61K 31/135
[52] U.S. Cl. .......................... 514/220; 514/282; 514/535; 514/653
[58] Field of Search .................................. 514/220, 282, 514/653, 535

[56] References Cited

U.S. PATENT DOCUMENTS

| | | | |
|---|---|---|---|
| 5,229,382 | 7/1993 | Chakrabarti et al. | 514/220 |
| 5,605,897 | 2/1997 | Beasley, Jr. et al. | 514/220 |
| 5,703,232 | 12/1997 | Bunnell et al. | 540/557 |

FOREIGN PATENT DOCUMENTS 9735586  10/1997  WIPO.

OTHER PUBLICATIONS

*The Merck Index*, abstract No. 6129, 1983.

Chemical Abstract 127: 288191 (abstract of WO 9735586), 1997.

*Primary Examiner*—Kevin E. Weddington
*Attorney, Agent, or Firm*—Arleen Palmberg; MaCharri Vorndran-Jones

[57] ABSTRACT

The present invention provides a method for providing anesthesia using a composition comprising olanzapine and one or more opioids.

15 Claims, No Drawings

ANESTHETIC METHOD AND COMPOSITION

This application claims the benefit of U.S. Provisional Application Ser. No. 60/014,120, filed Mar. 25, 1996.

FIELD OF THE INVENTION

This invention provides a method for using 2-methyl-4-(4-methyl-1-piperazinyl)-10H-thieno[2,3-b][1,5]benzodiazepine, (hereinafter referred as "olanzapine") and an opioid as an anesthetizing agent.

BACKGROUND OF THE INVENTION

This invention relates to a therapeutic combination of compounds to provide anesthetic activity.

Surprisingly, we have discovered that olanzapine can be particularly useful as an anesthetic when used in combination with one or more opioid compounds. More specifically, the invention provides a method of providing anesthesia in a mammal using olanzapine in combination with an opioid to provide such anesthetic effect.

There are opioid compounds known in the literature and to the skilled artisan. see Merck Manual, 16th Ed. (1992) p. 1409.

One of the key advantages possible with the method claimed herein relates to significantly reduced side effects associated with opioid compounds. The presently claimed combination provides benefits associated with post-surgical emergence from anestesia. Opioids are associated with undesired post-surgical side effects, which can be significantly alleviated using the combination claimed herein. With the current propensity toward outpatient surgery, the benefical properties of this combination could provide a valuable benefit for the patient. Further, the composition claimed herein can be especially useful during the presurgical preparation period, particularly if the patient is in pain.

It is known that olanzapine can provide antipsychotic activity. Olanzapine is a known compound and described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety. Surprisingly, and in accordance with this invention, Applicants have discovered that olanzapine can be useful as an anesthetic when administered with one or more opioids. An olanzapine:opioid composition could address a long felt need for a safe and effective anesthetic with fewer side effects.

SUMMARY OF THE INVENTION

The present invention provides a method providing anesthesia comprising administering to a patient in need thereof, an anesthetic composition comprising olanzapine or a pharmaceutically acceptable salt thereof; and one or more opioids in a weight ratio of olanzapine to opioids of from about one part olanzapine to from about one (1) part to about 1000 parts opioid.

A preferred composition is a weight ratio of olanzapine to opioids of from about one part olanzapine to from about 1 part to about 500 parts opioid.

Preferred opioid compounds are morphine, codeine, meperidine, methadone, propoxyphene, levorphanol, hydromorphone, oxymorphone, oxycodone, brompton's cocktail, fentanyl, alfentanyl, sufentanyl, and analogs there of, naloxone, naltrexone, pentazocine, butorphanol, nalbuphine, buprenorphine, fentanyl, alfentanil, sufentanil, carfentanil, and analogs thereof.

Particularly preferred opioids are selected from the group consisting of morphine, codeine, and methadone. Other particularly preferred opioids are selected from the group consisting of buprenorphine, fentanyl, alfentanyl, and sufentaryl.

Another particularly preferred group comprises of fenatanyl, alfentanil, sufentanil, and carfentanil.

The invention further provides a composition for providing anesthesia comprising olanzapine or a pharmaceutically acceptable salt or solvate thereof and one or more opioids in a weight ratio of olanzapine to opioids of from about 1 part olanzapine to about 0.01 parts to about 1000 parts opioid.

DETAILED DESCRIPTION OF THE INVENTION

Olanzapine is of the formula

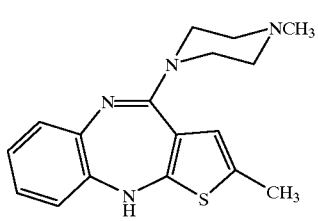

or an acid addition salt thereof.

It is especially preferred that olanzapine will be the Form II olanzapine polymorph having a typical x-ray powder diffraction pattern as represented by the following interplanar spacings:

d
10.2689
8.577
7.4721
7.125
6.1459
6.071
5.4849
5.2181
5.1251
4.9874
4.7665
4.7158
4.4787
4.3307
4.2294
4.141
3.9873
3.7206
3.5645
3.5366
3.3828
3.2516
3.134
3.0848
3.0638
3.0111
2.8739
2.8102
2.7217
2.6432
2.6007

A typical example of an x-ray diffraction pattern for Form II is as follows wherein d represents the interplanar spacing and I/I$_1$ represents the typical relative intensities:

| d | I/I$_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper K$_a$ radiation source of wavelength, 1=1.541 Å.

It is further preferred that the Form II olanzapine polymorph will be administered as the substantially pure Form II olanzapine polymorph.

As used herein "substantially pure" refers to Form II associated with less than about 5% Form I, preferably less than about 2% Form I, and more preferably less than about 1% Form I. Further, "substantially pure" Form II should contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water.

The polymorph obtainable by the process taught in the '382 patent will be designated as Form I and has a typical x-ray powder diffraction pattern substantially as follows, obtained using a Siemens D5000 x-ray powder diffractometer, wherein d represents the interplanar spacing:

d
9.9463
8.5579
8.2445
6.8862
6.3787
6.2439
5.5895
5.3055
4.9815
4.8333
4.7255
4.6286
4.533
4.4624
4.2915
4.2346
4.0855
3.8254
3.7489
3.6983
3.5817
3.5064
3.3392
3.2806
3.2138
3.1118
3.0507
2.948
2.8172
2.7589
2.6597
2.6336
2.5956

A typical example of an x-ray diffraction pattern for Form I is as follows wherein d represents the interplanar spacing and I/I$_1$ represents the typical relative intensities:

| d | I/I$_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper K$_a$ of wavelength 1=1.541 Å. The interplanar spacings in the column marked "d" are in Angstroms. The typical relative intensities are in the column marked "I/I$_1$".

The term "opioids" or "opioid", as used herein, shall refer to opioid analgesics and antagonists including natural opioid analgesics, synthetic opioid analgesics, opioid antagonists and opioid agonist-antagonists. Preferred opioid compounds are selected from, but in no way limited to, the group consisting of morphine, codeine, meperidine, methadone, propoxyphene, levorphanol, hydromorphone, oxymorphone, oxycodone, brompton's cocktail, naloxone, fentanyl, alfentanyl, sufentanyl, naltrexone, pentazocine, butorphanol, nabuphine, buprenorphine, fentanyl, alfentanil, sufentanil, and carfentanil. More preferred opioid compounds are selected from the group consisting of codeine, nabuphine, naloxone, fentanyl, alfentanyl, sufentanyl, and naltrexone. The term opioid shall refer to any compound acting at opioid receptors. Applicants appreciate that new opioids may be in development, and the present invention contemplates a synergistic composition comprising such new agents with olanzapine as well.

As used herein, the term "mammal" shall refer to the Mammalia class of higher vertebrates. The term "mammal" includes, but is not limited to, a human.

In the composition of this invention olanzapine or a pharmaceutically acceptable salt thereof and one or more opioids are combined in a weight ratio of olanzapine to opioids of from about one part olanzapine to from about 1 to about 1000 parts opioid.

A preferred composition is a weight ratio of olanzapine to opioid of from about 1 to about 500.

Olanzapine is effective over a wide dosage range; however, it is desirable to administer a dosage that is as low as possible. The amount of opioids present in the composition is adjusted as described above in ratio to the olanzapine dosage. For example, an anesthesia producing dosage of the olanzapine will normally fall within the range of about 1 mg to about 30 mg and the opioids in the composition would be from about 0.1 to 1000 times that amount. However, it will be understood that the amount of the compound actually administered will be determined by a physician, in the light of the relevant circumstances including purpose for anesthetising the patient, the choice of compound to be administered, the age, weight, and response of the individual patient, and the chosen route of administration, and therefore the above dosage ranges are not intended to limit the scope of the invention in any way.

The results of pharmacological studies show that olanzapine has muscarinic cholinergic receptor activity. The compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman et al Nature 216:717 (1976)) binding assays respectively. Further, olanzapine is active at the 5-HT-2 receptor and 5-HT2C (formorly knowm as 5-HT1C receptor) receptor. The complex pharmacological profile of the compound provides a medicament which can be useful as an anesthetic when administered with an opioid.

The dosage administered will, of course, vary depending on known factors such as the pharmacodynamic characteristics of the particular agent, and its mode and route of administration; age, health, and weight of the recipient; nature and extent of the anesthesia desired, kind of concurrent treatment, and the general effect desired.

A composition of this invention may be administered at a dosage to provide only mild anesthetizing effect for pre-surgical purposes. Such treatment may decrease anxiety, provide amnesia for the perioperative period while maintaining cooperation prior to loss of consciousness, and relieve preoperative pain, if it is present. Further, such administration during the perioperative period may reduce the need for inhalation anesthetic agent. Such composition may additionally provide an anti-emetic effect.

Compositions suitable for internal administration contain from about one half (0.5) milligrams to about 600 milligrams of active ingredient per unit. In these pharmaceutical compositions, the active ingredient will ordinarily be present in an amount of from about 0.5% to about 95% by weight based on the total weight of the composition.

Typical compositions include olanzapine or a pharmaceutically acceptable acid addition salt thereof and one or more opioids, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

The compositions of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human.

Utility Test Methods

The anesthetic activity of the composition of the invention is evidenced by tests intially conducted on rats. Male rats are fasted for 16–22 hours and weighed. Doses are coded using a code unknown to the observer.

Rats are anesthetized using a composition of this invention. The animals are observed for side effects, sufficiency of anesthesia, and for speed of recovery from anesthetic as well as the alertness of the animals.

The materials for the present invention can be purchased or prepared by a variety of procedures well known to those of ordinary skill in the art. Olanzapine can be prepared as described by Chakrabarti in U.S. Pat. No. 5,229,382 ('382), herein incorporated by reference in its entirety. Further, the following preparations illustrate a method for preparing of the especially preferred Form II olanzapine polymorph.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

Preparation 1

Technical Grade Olanzapine

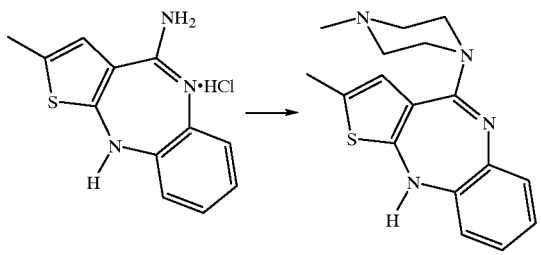

Intermediate 1

In a suitable three neck flask the following was added:
Dimethylsulfoxide (analytical): 6 volumes
Intermediate 1: 75 g
N-Methylpiperazine (reagent): 6 equivalents
Intermediate 1 can be prepared using methods known to the skilled artisan. For example, the preparation of the Intermediate 1 is taught in the '382 patent.
A sub-surface nitrogen sparge line was added to remove the ammonia formed during the reaction. The reaction was heated to 120° C. and maintained at that temperature throughout the duration of the reaction. The reactions were followed by HPLC until 25% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.
Yield: 76.7%; Potency: 98.1%

Preparation 2

Form II Olanzapine Polymorph

A 270 g sample of technical grade 2-methyl-4-(4-methyl-1-piperazinyl)-10H-thieno[2,3-b][1,5]benzodiazepine was suspended in anhydrous ethyl acetate (2.7 L). The mixture was heated to 76° C. and maintained at 76° C. for 30 minutes. The mixture was allowed to cool to 25° C. The resulting product was isolated using vacuum filtration. The product was identified as Form II using x-ray powder analysis.
Yield: 197 g.

The process described above for preparing Form II provides a pharmaceutically elegant product having potency $\geq 97\%$, total related substances <0.5% and an isolated yield of >73%.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), opioid (3% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

We claim:

1. An anesthetic composition comprising (1) olanzapine, or a pharmaceutically acceptable salt or solvate thereof, and (2) an opioid; wherein the weight ratio of olanzapine to opioid is about 1 part olanzapine to about 0.01 to about 1000 parts opioid.

2. A composition of claim 1 wherein the olanzapine is Form II olanzapine polymorph.

3. A composition of claim 1 wherein the weight ratio of olanzapine to opioid is about 1 part olanzapine to about 1 to about 500 parts opioid.

4. A composition of claim 1 wherein the opioid is selected from the group consisting of morphine, codeine, meperidine, methadone, propoxyphene, levorphanol, hydromorphone, oxymorphone, oxycodone, brompton's cocktail, naloxone, naltrexone, pentazocine, butorphanol, nabuphine, buprenorphine, fentanyl, alfentanil, sufentanil, and carfentanil.

5. A composition of claim 2 wherein the opioid is selected from the group consisting of codeine, nabuphine, naloxone, fentanyl, sufentanyl, alfentanyl, buprenorphine, and naltrexone.

6. A composition of claim 3 wherein the weight ratio is 1 part olanzapine to from about 1 to about 100 parts opioid.

7. A method for anesthetizing a mammal comprising administering an anesthetizing dose of a composition comprising (1) olanzapine, or a pharmaceutically acceptable salt or solvate thereof, and (2) an opioid; in a weight ratio of olanzapine to opioid of about 1 part olanzapine to about 0.1 to about 1,000 parts opioid.

8. A method of claim 1 wherein the opioid is selected from morphine, codeine, meperidine, methadone, propoxyphene, levorphanol, hydromorphone, oxymorphone, oxycodone, brompton's cocktail, naloxone, naltrexone, pentazocine, butorphanol, nabuphine, buprenorphine, fentanyl, alfentanil, sufentanil or carfentanil, or a pharmaceutically acceptable salt thereof.

9. A method of claim 8 wherein the weight ratio of olanzapine to opioid is about 1 part olanzapine to about 500 parts opioid.

10. A method of claim 9 wherein the olanzapine is Form II olanzapine polymorph.

11. A method of claim 10 wherein the opioid is codeine, nabuphine, naloxone, fentanyl, alfentanyl, sufentanyl, or naltrexone.

12. A method of claim 7 wherein the anesthetizing dosage provides mild pre-surgical anesthesia.

13. A method of claim 12 wherein the composition is administered during the perioperative period to provide amnesia while maintaining cooperation.

14. A method of claim 7 wherein the mammal is a human.

15. A method of claim 13 wherein the mammal is a human.

* * * * *